United States Patent [19]

Sair et al.

[11] 4,230,687

[45] Oct. 28, 1980

[54] ENCAPSULATION OF ACTIVE AGENTS AS MICRODISPERSIONS IN HOMOGENEOUS NATURAL POLYMERIC MATRICES

[75] Inventors: Louis Sair, Evergreen Park; Ralph A. Sair, Lincolnwood, both of Ill.

[73] Assignee: Griffith Laboratories U.S.A., Inc., Alsip, Ill.

[21] Appl. No.: 910,101

[22] Filed: May 30, 1978

Related U.S. Application Data

[63] Continuation-in-part of Ser. No. 779,463, Mar. 21, 1977, abandoned, and Ser. No. 719,740, Sep. 2, 1976, abandoned.

[51] Int. Cl.³ .................. A01N 25/28; A61K 9/26; A61K 31/07; B01J 13/02
[52] U.S. Cl. .................................. 424/22; 252/316; 424/34; 424/35; 424/36; 424/37; 424/344; 426/72; 426/73; 426/89; 426/96; 426/102; 426/103; 426/311; 426/534; 426/548
[58] Field of Search .............. 252/316; 424/22, 36, 424/344; 426/89, 96, 102, 103, 534, 548

[56] References Cited

U.S. PATENT DOCUMENTS

| | | | |
|---|---|---|---|
| 2,876,160 | 3/1959 | Schoch et al. | 426/98 X |
| 2,933,392 | 4/1960 | Iacono et al. | 424/344 X |
| 3,780,195 | 12/1973 | Balassa | 252/316 X |
| 3,857,964 | 12/1974 | Yolles | 426/96 X |
| 3,922,354 | 11/1975 | Galluzzi et al. | 426/578 X |
| 3,962,416 | 6/1976 | Katzen | 426/103 X |
| 3,968,268 | 7/1976 | Sair et al. | 426/580 |
| 3,971,859 | 7/1976 | Huessy | 426/618 |
| 3,978,244 | 8/1976 | Sair | 426/656 X |
| 3,985,913 | 10/1976 | Johnson et al. | 426/103 X |
| 4,065,578 | 12/1977 | Reggio et al. | 426/548 X |

*Primary Examiner*—Richard D. Lovering
*Attorney, Agent, or Firm*—Kegan, Kegan & Berkman

[57] ABSTRACT

A method for effectively encasing an active agent such as a chemical compound, a seasoning, a flavoring, or a nutrient such as vitamins and minerals, including liquids, as a time-stable but releasable dispersion in a homogeneous polymeric encapsulating matrix of a modified starch, a gum or a protein material such as gelatin and casein to provide a concentrate of the active agent. The method is characterized in that the agent to be encased is mixed with the encapsulating material under conditions of rigorous and intimate mechanical working with applied high shearing stress but without phase-separating mechanical compression and compaction forces and in the presence of a limited quantity of water and sufficient heat to ensure the formation of a viscous, semi-solid, homogeneous paste constituting a mobile mass or plastic melt. The melt, consisting of a homogeneous matrix with the encased agent distributed therethrough as a microdispersed phase, is then formed into any desired shape, while avoiding phase-separating compaction and compression forces, and dried to provide a product stable against loss and deterioration of the encased agent. In a preferred embodiment of the invention the encased agent is gradually released from the enveloping matrix at a rate dependent on the rate of hydration of the matrix.

15 Claims, 1 Drawing Figure

ENCAPSULATION OF ACTIVE AGENTS AS MICRODISPERSIONS IN HOMOGENEOUS NATURAL POLYMERIC MATRICES

This application is a continuation-in-part of Sair & Sair application Ser. No. 779,463 for "ENCASEMENT OF FLAVORING AND NUTRIENT AGENTS IN PROTEIN MATERIALS", filed Mar. 21, 1977, and now abandoned and Sair and Sair application Ser. No. 719,740 for "ENCASEMENT OF FLAVORING AND NUTRIENT AGENTS IN CARBOHYDRATE MATERIALS", filed Sept. 2, 1976, and now abandoned and the entire disclosure of each of these applications is hereby incorporated herein by reference, to the extent not inconsistent herewith.

BACKGROUND OF THE INVENTION

The food and related industries have long been seeking new and improved products and techniques whereby edible materials such as seasonings, coloring agents, flavorings and nutrients, particularly liquid agents, may be encased, encapsulated or otherwise embedded, dispersed, or contained in protective enveloping media, for subsequent release. The methods which have been used to achieve encapsulation fall in several broad groups. Some processes call for forming solutions or aqueous emulsions of the agent to be encapsulated with an encapsulating medium such as gum acacia or amylodextrins. The aqueous system is then spray dried to form film-engulfed globule-like particles which contain enveloped material. While this procedure has produced encapsulation, the technique calls for high energy input. Moreover, since the final product is invariably a fine powder, the product has somewhat limited utility.

Another technique has been to solubilize a material such as gelatin to provide a solution. A flavor oil, nutrient or other edible agent is then added with suitable agitation to effect emulsification or dispersion and the system is cooled to form a solid gel. Thereafter, the gel is dried, and then ground. This procedure requires special drying apparatus and carefully controlled drying conditions.

Still other methods use sugar melts as protective coatings. Related processes use carbohydrate materials other than gums or amylopectins, for example, starches. The starch must first be gelatinized, a process in which a substantial ratio of water to starch is employed to produce a starch paste. The flavorings or nutrients are then emulsified in the paste, followed normally, by spray drying. The gelatinized starches are viscous, presenting handling and drying problems.

Spray drying has been the most widely employed technique for the encapsulation of products used in the food industry. However, this process has very serious shortcomings. These are indicated in the comments of Balassa in U.S. Pat. No. 3,780,195:

> The elevated temperatures used in spray drying operations tend to volatilize all or part of the most volatile components of the active material. This is a particularly serious problem when the active material comprises very volatile materials such as flavoring oils. The elevated temperatures of the spray drying process also tend to degrade any heat sensitive active materials. If the capsule composition is sprayed into air, there is the danger of oxidizing any oxidation prone materials.

It is an important feature of the present invention that it eliminates the above-indicated deficiencies of the spray drying technique. The process facilitates encapsulation, utilizing a relatively simple procedure in which the water concentration is controlled. Hydrophilic polymers such as natural gums, modified starches and proteins are processed to produce a heavy, viscous paste which is subjected to vigorous agitation and shear so that the material to be encapsulated, including essential oils, food flavors, fragrances, agricultural chemicals such as insecticides, or medicinal compounds such as vitamins and drugs may be distributed throughout the viscous, homogeneous encapsulating material which then serves as a protective matrix for the very finely sized particles of the encased agent, constituting the dispersed phase. The viscous paste is then sheeted on a chilled roll, or otherwise formed and partially dried at relatively low temperatures. Finally, the semi-dried product is ground, followed by any additional drying which may be desired.

It is an important discovery of the present invention that there is no need, in achieving encapsulation, completely to solubilize the protein, gum, or modified starch. A solution, in the usual sense, is not required. The encapsulation can be effected mechanically utilizing the encapsulating material in a homogeneous gel or gel-like form.

A related feature of the invention is that a markedly reduced concentration of water is possible, thus effecting material savings in the energy normally required to dispel the moisture from the final product.

Yet another feature of the invention is that the encapsulation may be carried out at relatively low temperatures. For example, in the encapsulation of a compound such as acetaldehyde, a temperature in the range of about 40° F. is used, followed by sheeting and drying. The method of the invention effects conversions of up to about 40% as contrasted with only about 1 to 5% for conventional prior art procedures. Encapsulation of butter flavors containing diacetyl and butyric acid is conducted at temperatures of about 160° F., below the boiling point of diacetyl, so there is essentially 100% conversion. Again, this is in marked contrast with conventional prior art procedures in which there are great losses in the butter flavor elements.

Based upon the teachings of the present invention, it will be appreciated that when encapsulating an essential oil, such as oil of clove, having a much higher boiling point, emulsification can be carried out at still higher temperatures and drying at proportionally higher temperatures.

A very important feature of the process of the present invention is its versatility. The process may be carried out effectively using such diverse materials as proteins, gums and modified starches. The selection of a particular encapsulating material as the protective matrix is dictated by the ultimate contemplated application. For example, if one wishes to utilize the encapsulated product in a cake mix where the level of moisture is high and where it is desired to retain the flavor during the baking process, one could use a matrix derived from a proteinaceous material, which is less soluble than other matrices, so that the flavor element is liberated more slowly, as the hydration of the protein progresses. In products such as cookies there is insufficient moisture to effect hydration of a proteinaceous matrix. Accordingly, a gum or modified starch encapsulating medium is preferred.

A majority of the encapsulated products used in food today are produced through spray drying techniques. Schock U.S. Pat. No. 2,876,160 describes the use of various modified starches as encapsulating films in spray drying procedures. It is significant that Schock teaches that the viscosity of the solution to be used in the process be 50 centipoises or less, the ratio of water to the matrix material being relatively high. In the practice of the present invention it has been found that when using a modified starch such as Capsul (National Starch and Chemical Co.) as the encapsulating material, the desired gel is produced by using 15 parts of water to about 80 parts of the modified starch. In contrast, for spray drying, about 120 parts by weight of water is used to 80 parts by weight of Capsul.

There are many facets of and parameters pertaining to the process and to the raw materials used in practicing the present invention. Relevant to the efficacy of a particular product for a specific use are the encapsulating or encasing medium, the "active" agent to be encased, the water concentration, the temperature and the viscosity of the mixture during the applied shearing stress and mechanical working, the forming or shaping of the paste-like product, the pre-drying, and the final drying and sizing of the ultimate product to provide the desired granulation. All of these variables affect the formulation of the homogeneous matrix, the nature of the completeness of the microdispersion, and the stability of the final product in shelf storage.

The matrix material may, in accordance with the invention, be a protein such as casein, gelatin or wheat gluten. Each is hydrophilic and each reacts in aqueous systems (at variable rates) to form viscous hydratable products. Alternatively, the matrix material may be a gum or modified starch, each characterized in being capable of forming stable, viscous, homogeneous pastes with relatively low concentrations of water, and each receptive to the distribution of the active agent therethrough as a microdispersion.

If the final product is to be incorporated in a chewing gum, a slow release of the active agent is the goal. Accordingly, the use of a protein is dictated, since proteinaceous materials are ordinarily less soluble and the rate of release of the encased agent is dependent upon the rate of hydration of the engulfing matrix. For some applications it is imperative that the ultimate product in which the composition of the invention is incorporated be dissolvable to form a clear solution. Specific encasing agents must be selected to achieve this goal. No single encapsulating material is suitable for all purposes, and in some applications, a combination of two matrix materials, such as proteins and modified starches may be desirable. Since some modified starches contribute flavor to the ultimate products, a gum matrix such a gum acacia may be preferred.

The active agent or agents to be encased in the matrix may be any of many materials including but not limited to flavorings, perfumes, oleoresin, vegetable oils, vitamins, sugar, flavor potentiators, such as acetaldehyde, delicate butter flavors and chemicals such as insecticides. In substance, the encased agent may be any compound which may be rendered more suitable for use or more convenient in a particular system, either by reason of minimizing oxidation, controlling release of the encased material, preventing flavor deterioration on storage, or for any other useful purpose.

In carrying out the process of the invention, the concentration of water relative to the concentration of encasing material is critical, but does not lend itself to precise mathematical definition. The quantity of water should be only sufficient to produce a viscous paste with the encapsulating material so that the active agent can be distributed as a microdispersion throughout the resulting homogenous matrix. Empirically, it has been found that suitable operating viscosities range from about 50,000 to about 1,000,000 centipoises or more. It is required that the product be firm but flowable and that the water be adequate to ensure sufficient hydration of the matrix material to permit the establishment of the microdispersion in a homogeneous encapsulation medium.

The process of the invention embraces a broad temperature range extending from below room temperature to near the boiling temperature of water. To a marked degree, the temperature used is dictated by the physical and chemical properties of the agent to be encased. For example, acetaldehyde is encapsulated at a temperature well below its boiling point of 78° F., butter flavors in the temperature range of about 150° F., and essential oils such as oil of clove at a temperature of about 185° F.

A key and controlling step in the process of the invention relates to "shear". While the precise apparatus to be used in achieving this shearing action is not critical, it has been found that a plow mixer similar to a Littleford is quite efficacious. This machine provides a hurling, whirling action produced by the movement of plow-shaped mixing tools causing intense but controlled intermingling of the component elements of the mix. High speed chopper blades break up any agglomerates. Other suitable equipment includes the Baker Perkins Ko-Kneader blender which provides high shear and high intensity mixing of the viscous mass without development of compression or compaction forces.

A characterizing feature of the processing system of the subject invention is its high viscosity. Using appropriate equipment, such as plow mixers, it is possible, in accordance with the invention, to develop sufficient resistance in the viscous mass so as to effect the required dispersion of the active agent throughout the encapsulating medium. Conventional solutions and low viscosity mixtures or pastes are avoided, as are systems which are adapted for spray drying. The viscous mass produced in accordance with the invention is such that it may promptly be shaped or formed into sheets or rods, on chilled rolls or other suitable equipment.

Not all parameters which control the efficacy of the forming operation are completely know, but it has been established that the product discharged from the agitator must not be too sticky and must have sufficient physical integrity in a relatively thin sheet, rod, or other shape so that it may be conveyed to a suitable dryer while retaining, generally, its shape and form. The encapsulating medium must be homogeneous. This is critical. Control of the moisture content during dispersion formation is very important. Care is taken not to drive off substantial amounts of water during this critical step.

A modified starch (Capsul)* has been found to form an excellent matrix in a system in which about 5 pounds of water is used for each 20 pounds of the Capsul, to encapsulate about 20% by weight of an active agent such as an essential oil. The viscous mass has a viscosity in excess of 1,000,000 centipoises when it leaves the reactor. This product sheets readily and can then be dried without significant loss of the microdispersed active material. If in the same type of system, the water concentration is increased to 25% (based on the total of the modified starch and the water) the resulting product is much more fluid, and it becomes extremely difficult to form the desired sheet using chilled rolls. If the water concentration is increased somewhat more (7 pounds of water to 20 pounds of Capsul), to a concentration of about 26%, upon addition of 20% of active agent (based on the total weight of encasing agent and active agent), the resulting mixture is fluid with a viscosity of about 34,000 centipoises. This too-fluid material could not be effectively formed or shaped into a film or sheet.

*National Starch and Chemical Corp.

The optimum concentration of water will, of course, vary with the particular type of encapsulating medium used. For example, for gum acacia, a preferred water concentration is about 37.5% by weight or 11 pounds of water to about 20 pounds of gum acacia. This ratio makes it possible to achieve the required viscosity for effective sheeting. If the water concentration is increased to about 41% (14 pounds of water to 20 pounds of gum acacia), the resulting mixture is a fluid with a viscosity of only about 16,000 centipoises. This product could not be sheeted effectively or formed.

Once the sheet consisting of the homogeneous matrix with the active agent dispersed therethrough as micron particles is formed, it is conveyed through a suitable drying tunnel and pre-dried at a temperature in the range of about 110° F. to about 150° F. with a high velocity air stream so that within about two to ten minutes sufficient moisture has been dispelled to render the sheet somewhat brittle. It is then physically broken into smaller pieces using equipment such as a Comitrol chopper. The smaller pieces can then be dried further, followed by grinding. It has been found advantageous to reduce the size of the sheets when the product itself still contains 10 to 20% moisture. The coarsely ground material is then subjected to final drying and further grinding if desired. In some applications, the predrying step is not necessary. The procedure outlined is effective to minimize fissure points, facilitating the final grinding and producing products with enhanced conversion and stability.

The selected degree of granulation for the finished product is affected by the contemplated end use. For example, if the product is to be incorporated in chewing gum, where grittiness is to be avoided, the final product is finely ground, normally to pass a 100 mesh screen. Conversely, a product to be used in bath salts is ground very coarsely. Since the rate of flavor release is dependent, in part, on the "mesh" of the final product, in some applications the product is ground through a 10 mesh screen, in others a 40 mesh screen, or even finer. An advantage of the invention is its simple flexibility particularly as to the specific size of granules to be achieved in the final preparation. In contrast, the spray drying technique of the prior art provides no corresponding option. The spray dried product is always a very fine powder.

In accordance with the practice of the invention, certain modified starches are suitable as encapsulating agents; others are not.

In spray drying, the ratio of water to the encasing agent is evidently sufficient to render many modified starches suitable as the enveloping film material. In contrast, in the method of the present invention it has been found that the selection of a suitable modified starch is critical since some of these products such as Capsul are suitable while others, for example, Nadex 772, which is also made by National Starch and Chemical Corporation, did not provide a good micro-dispersion, and when the product was sheeted free essential oil was expelled. Free essential oil was also found in the mixer. Yet, this same product is described as excellent for use in the production of spray dried products, and shows good stability against oxidation. An additional modified starch, also found to be excellent in spray drying processes is National 46. Again, this particular modified starch does not function well in the practice of the present invention.

One additional modified starch which has been found to be suitable in the practice of the invention is identified by the brand name Purity Gum BE. The modified starch formed a functional viscous mass when combined with 23% water, and the system provided good encapsulation and products of excellent stability.

The chemistry of modified starches is extremely complex, and much of the pertinent information is maintained as trade secrets. However, it has been possible to relate some of the available information to determine functionality as it relates to the subject invention. Based upon the teachings of the invention as set forth herein, those skilled in the art will be able to determine with a minimum of "experimentation" and with simple tests which modified starches are functional and which are not.

In the efficient and practical practice of the invention, one goal is to convert 90% or more of the essential oil into the finished product. In working with very volatile materials such as acetaldehyde, a conversion of 40% is sought. In the encapsulation of butter flavors, the conversion of materials such as butyric acid and diacetyl is essentially quantitative. Regarding the stability of the ultimate products the goal of the invention is 90% or better.

One prior art process for the production of artificial spice particles is described in Galluzzi et al U.S. Pat. No. 3,922,354. That process is materially different from the process of the present invention, and the products of Galluzzi are readily distinguishable from the products of the instant invention. Galluzzi forms a "difficulty flowable mash" using gelatinized cereal solids as the major component, heats the mass until some gelation takes place, while the water concentration is reduced from about 30% to about 15%, cools, and then adds a flavoring agent to the cooled mass, with agitation. Finally, the Galluzzi product is further cooled to harden, and the hardened mass ground. As expressly taught by Galluzzi and as clearly illustrated in the drawing of the Galluzzi patent, the flavoring agent is "dispersed" in a heterogeneous matrix consisting of 2 components. One is the hardened gelatined material, and the other component consists of physically distinct "chucks" of insoluble farinaceous material constituting the ungelatinized cereal solids. Isolated pockets or globules of the flavoring agent are shown in this heterogeneous matrix.

Galluzzi produces no microdispersion of flavoring agent in the sense of the instant invention. This fact is clear from a consideration of the Galluzzi specification and from the patent drawing, a 120X magnification of Galluzzi's artificial spice particle. The Galluzzi flavoring agent globules are much larger than the micron-submicron particles of the dispersed phase of the subject invention. They do not constitute a microdispersion in a homogeneous matrix.

In fundamental contrast with the method and products of Galluzzi et al, the active agent of the present invention is dispersed as micron size and sub-micron particles throughout a homogeneous matrix. The instant system is a two component system rather than the three component system of Galluzzi et al. Moreover, tests carried out to compare the products produced establish conclusively that the flavor agents of Galluzzi are not encased and protected as they are in the present invention. There is substantial loss of essential oil from the "matrix" upon incubation of the Galluzzi product. After four days at 100° F., essential oil losses ranged from 50% to 83%. For products made in accordance with the present invention, the losses were only 5 to 10%, under the same test conditions. The flavor oil does not act as truly encapsulated in the Galluzzi product. Rather, the oil is an unprotected component of a heterogeneous system.

SUMMARY OF THE INVENTION

In applicants' prior application Ser. No. 719,740, now abandoned two encasement processes are described. One uses an extrusion technique under conditions to produce a dense, glassy, storage-stable extrudate containing an enveloped but recoverable edible material. This extrusion process is not completely satisfactory as a method for encasement of relatively large concentrations of a liquid such as an essential oil. The relatively high pressure and the compression and compaction forces imposed on the system during extrusion causes the oil or liquid phase to be expelled physically, thus significantly limiting the upper concentration of liquid which can be encapsulated. The second process described in parent application Ser. No. 719,740, now abandoned and in parent application Ser. No. 779,463, now abandoned is to prepare a physical dispersion of a flavoring agent, essential oil or nutrient in a carbohydrate material, gum, or proteinaceous melt under conditions of rigorous and intimate mechanical working with applied high shearing stress in the presence of a limited quantity of water. A viscous, semi-solid, plastic melt is formed in which a relatively high concentration of the encased material is effectively established as a microdispersed phase. The melt is then formed into any desired shape and dried. It is to the latter method and to the products produced thereby that the subject application is directed.

In accordance with the practice of the present invention, it has been found possible, through the application of high shearing stress in the presence of limited water, to encase or encapsulate a high concentration of an ingestible liquid agent as a dispersed phase is a melt. The product may then be formed directly on chilled rolls, followed by suitable drying.

It is an important feature of the present invention that excellent encasement of agents such as essential oils may be achieved through the use of as little as 1 part or less of water to 4 parts of encapsulating material.

In accordance with the practice of the invention, the material to be encased, for example, an essential oil or oleoresin, is dispersed in a gum, modified starch or proteinaceous melt by agitating under conditions of rigorous and intimate mechanical working with accompanying high shearing stress in the presence of a limited quantity of water to form a viscous, translucent, semi-solid, homogenous mass which may then be formed and dried to provide a dispersion of the ingestible agent in an enveloping protective matrix.

An advantage of the process of the present invention is that drying may be carried out at any desired temperature, including relatively low temperatures, so as to minimize losses of important volatile constituents. Flavors such as essential oils contain many compounds which vaporize at low temperatures but are very important in contributing to the overall flavor and aroma of the compound. In spray drying many of these finer flavors and aromas are lost, and the aromatic profile is destroyed. An advantage of the process of the present invention is that by drying at relatively low temperatures, the finer flavor and aroma constitutents are retained so that the encapsulated product has not been changed in character as compared with the agent being encapsulated. The detrimental high drying temperatures used in spray drying are avoided.

It is a related feature of the invention that the dried product containing essential oil as a microdispersion may be ground or otherwise rendered particulate to provide an end product in which the flavor oil component is atmosphere-protected and maintained in a time-stable condition.

In accordance with the practice of the present invention encasement of edible material in the protective homogeneous matrix is achieved without the use of pressure as in an extrusion process, and without compression and compaction. Unexpectedly and surprisingly, through vigorous working and shearing mixing the oleoresin, flavor oil or other liquid agent becomes a microdispersion in an enveloping homogenous carrier, without the need to form a solution of the encapsulating agent. The method of the invention disperses the liquid agent as microdroplets throughout a homogeneous protective matrix, without any need fully to dissolve the encapsulating agent.

In contrast to encapsulation through spray drying in which the final products consist of very fine particles only, the present invention makes it feasible to produce encapsulated products of any desired granulation or particle size distribution.

It is a related feature of the invention that the products which can be effectively produced are products in which the flavoring strength or concentration may be any selectible value, including values many times those of the flavoring strengths of the "natural" products or of the conventional "soluble seasonings". The encased agent may be present in the final product at a concentration of from 3% or less to about 80% or more.

The method of the invention is suitable for producing "simulated" natural spices and flavoring materials. The products may be used in food and food preparations in the same manner in which their natural counterparts are used, but have many advantages. The invention also contemplates the incorporation of coloring agents where such agents contribute to the desired appearance of the final product.

An additional important feature of the products of the invention is that selected encasing or matrix material may have a markedly lesser water solubility than do many of the encapsulating agents used in the prior art. As a result, the essential oil or other "active" agent in the encasement system is released and distributed more slowly when added to an aqueous system. That is, the present invention provides products which exhibit a gradual, extended and more controlled flavor release.

The essence of the present invention is the discovery of a new technique or method for producing a product which is also new. The method itself, though possibly simple in retrospect, invokes a new concept. In accordance with the present invention an active agent including a liquid, is effectively distributed as a microdispersion substantially uniformly throughout a homogeneous, encapsulating material which serves as a matrix for the dispersed components. In carrying out the method, the encasing material may be transformed into a "melt" through heat in the presence of a minimal quantity of water, from about 10% up to about 60%.

The method of the invention differs markedly from prior art encasement or encapsulation techniques which utilize solutions, conventional emulsions, and spray drying procedures.

An important feature of a preferred embodiment of the invention is that the enveloping phase or matrix is hydratable to release the encased material over a sustained, selectible time, dependent upon the particular matrix used.

The singe FIGURE of the drawing in this case is a print of a photomicrograph (315 X) illustrating micron-size particles of a flavoring oil dispersed in a homogeneous matrix, in accordance with the practice of the present invention. As shown, the dispersed phase constitutes minute globules distributed substantially uniformly throughout a homogeneous matrix.

Figure 1:
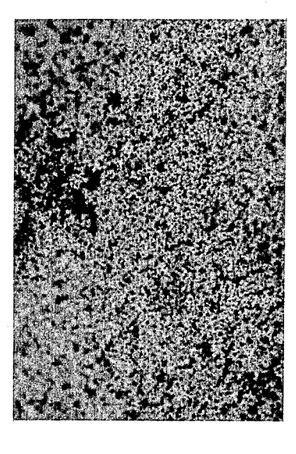

In order more fully to understand the properties of the products produced in accordance with the invention, formed sheets were prepared using both a proteinaceous (casein) and a modified starch material (Capsul) as the encasing matrix. In the case of the modified starch, the water concentration was 20% based on total weight of water and Capsul, and 20% by weight of essential oil was incorporated (based upon the total weight of essential oil and modified starch material). In the protein samples, 46% by weight of water was used and 20% essential oil.

A microscopic examination was carried out on a sample of the protein sheet. A protein of the sheet was first fixed in 10% formalin for 24 hours and then well rinsed in water. The fixed sheet was frozen at $-20°$ C. and then sectioned at 10 micron thickness. The sections were deposited on room temperature slides, air dried, and then stained with Oil Red O (250 mg. of dye per 100 cc of 99% isopropanol, and diluted with water and filtered prior to use). The stained section was covered, using glycerol and a cover slip, and examined at magnifications from 60 X to 160 X. At the lower magnification, the protein matrix appeared as a homogeneous phase in which the essential oil droplets were distributed uniformly. At the 160 X magnification, the protein melt appeared as a solid homogeneous background with uniformly distributed oil droplets therethrough. Measurement of the droplets or dispersed phase (using an eyepiece micrometer at 630 X) established that they range from about 2 microns to 0.2 micron or less in size. The spherical droplets were very closely spaced and appeared as a uniformly distributed phase.

Further microscopic studies of the protein matrix and the starch matrix products yielded "release" information. When water ws added to the modified starch products there was an immediate "explosive" release of the encased particles into the surrounding media, as "jet stream". Within one minute the sample was engulfed by a milky phase of released encased material, and an apparent equilibrium established. In contrast, when water was added to $\frac{1}{8}"\times\frac{1}{4}"\times\frac{1}{4}"$ pieces of protein sheet, the reaction was distinctly slower, as viewed under 7X magnification. There was virtually no release during the first minute. Then a slow moving stream developed. After 4 minutes, the "release" of the encased material from the protein matrix was still progressing and appeared equivalent to what was seen in the starch matrix at about 5 seconds. To summarize, in the case of modified starch, when water was added, the release of the encased material was explosive. For the protein product, the release was slow and ordered.

The examples set forth below are illustrative of the method of the invention and the products produced thereby. These examples are not to be construed in any limiting sense, the scope of the invention being defined in the appended claims.

DETAILED DESCRIPTION OF PREFERRED EMBODIMENTS

The present invention relates to a process in which a polymeric material derived from natural substances such as casein, a gelatin, modified starches, gums and related materials is mixed with an active agent such as a nutrient, seasoning, essential oil, flavoring agent, mineral, chemical compound, vitamin, or sweetener, and optional additional ingredients in the presence of a limited quantity of water in the range of from about 10 to about 65% by weight. The blend is mechanically worked under high shearing stress, to form a semi-solid, viscous mass in which the agent becomes a microdispersed phase in an enveloping homogeneous matrix. The process is carried out so as to avoid mechanical expulsion of the ingestible agent. The viscous mass may then be formed into any desired shape, and dried. Optionally, the final product may be ground to provide a particulate product.

It will be understood from the following detailed description that the method of the invention is effective to encapsulate many different types of active agents in various encapsulating materials and over a broad range of concentrational ratios of encapsulating material to active agent. In the illustrative examples provided herein, the ratio of encapsulating material to active agent, in parts by weight, embraces the range of from about 1 to 1/25th (Example 1) to about 1 to 5 (Example 21), and the water concentration covers from about 10 percent (Example 21 and 28) to about 50 percent (Example 1).

The aims and objects of the invention can be accomplished through the use of conventional equipment including commercially available mixers. Accordingly, no detailed description of apparatus is provided herein. However, the following examples are described with reference to various types of suitable equipment.

USE OF A SILENT CUTTER

The concept upon which this invention is predicated is that it is possible under conditions of intense shear or mechanical stress and using minimal water to encase a liquid phase as a microdispersion in polymer matrices derived from natural products. In order to explore this theory, initial work was carried out using a laboratory "silent cutter" or chopper, equipment which has been widely used in the meat industry as a blender and chopper to form meat emulsions such as sausage emulsions. A silent cutter includes a bowl which turns in a horizontal plane, and a series of vertically-supported rotating blades. According to the established techniques, chunks of meat, with fat, along with added moisture and salt, are added to the bowl and the mass forced continuously into the cutting paths of the multiple rotating blades. This action reduces the size of the meat and the fat and provides a substantially uniform meat emulsion in which the soluble protein of the meat surrounds the emulsified fat globules.

In the practice of the present invention, the same equipment was successfully used to produce an intimate blend of the encapsulating, matrix-forming material, e.g. casein, with an ingestible ingredient, e.g. an essential oil, to be encased, in the presence of minimal quantities of water. As described in Example I (TABLE I), 425 grams of casein, preheated to 100° F., was added to the bowl of the chopper together with 75 grams of oil of orange, preheated to 180° F. followed by the addition of 450 grams of boiling water. The mixture was blended for about 30 seconds after which 33 grams of 50% sodium hydroxide was added. A viscous, non-flowable but shapeable, semi-solid, translucent, gel-like proteinaceous mass was produced. No free essential oil was evident.

Operation of the chopper was continued until the material had been subdivided into pieces sized so that substantially all passed through a ¼" screen. The screened product was air dried for 4 days at room temperature to a moisture content of 6% by weight. Separate portions were then stored in open trays for 4 days and for 2 weeks at 100° F. after which samples were analyzed by distillation to determine essential oil loss. After the two week period, 92% of the essential oil remained in the product. The data are tabulated in TABLE I.

A similar procedure was carried out with the silent cutter, but using soy flour in place of casein. 425 grams of solvent extracted soy flour having an NSI of about 80% and a protein content of about 50% was added to the bowl of the chopper together with 75 grams of oil of orange and blended for about 30 seconds. 375 grams of boiling water was added and the mix blended until uniform, after which 11 grams of 55% sodium hydroxide was added to provide a visous, plastic, non-flowable but shapeable, semi-solid, sticky, proteinaceous mass, with no free oil of orange evident.

The chopping operation was continued until all the material was mechanically subdivided into pieces such that substantially all passed through a ¼" screen. As in Example 1, the screened product was air dried to about 6% moisture. Separate aliquots were stored for various periods at 100° F., and then analyzed to determine essential oil losses. After 2 weeks at 100° F., 54% of the oil remained in the product.

In a third run, using soy flour (Example 3) and oil of orange as in Example 2, it was found that 79% of the original oil content of the product remained in the product after two weeks' storage at 100° F., all as summarized in TABLE I.

TABLE I

| | SILENT CUTTER | | |
|---|---|---|---|
| Example No. | 1 | 2 | 3 |
| Casein (gms) | 425 | — | — |
| Soy Flour (gms) (90% NSI) | — | 425 | 426 |
| Water (gms) | 450 | 375 | 275 |
| Water (%) | 51 | 46 | 38 |
| 50% NaOH (ml) | 33 | 11 | — |
| Essential Oil Used (Oil of Orange)* | 15 | 15 | 15 |
| Essential Oil in Ground Dried Product (%)* | 10.8 | 9.2 | 6.6 |
| Fraction of Original Oil Used Found in Dried Product (%) | 72 | 61.3 | 44 |
| Essential Oil Retained in Product After 2 Weeks' Storage at 100° F. (%)* | 10.0 | 5.0 | 5.2 |
| Stability on Storage (%)** | 92 | 54 | 79 |

*Based on combined weight of protein material plus essential oil
**Based on essential oil content of ground dried product as originally produced.

In the examples recorded in TABLE I, it was found that the intimate chopping or mixing of the silent cutter distributed the essential oil as a protected, preserved microdispersion throughout the semi-solid proteinaceous mass or matrix. Suprisingly, it was discovered that a relatively high concentration of essential oil could be effectively dispersed in a heavy, semi-solid mass using only one part of water to one part of casein and that the oil would remain dispersed as a stable system.

The lower oil retention of the soy flour products as compared with the casein product was believed to be due to difficulty in providing adequate heating of the mix in the silent chopper equipment, there being no satisfactory method of heating the contents during the chopping operation. This problem was solved through the use of other equipment.

USE OF AN AUTOCLAVE

Although the silent cutter established the efficacy of the method of the invention, the equipment, lacking a cover and an external temperature control, was impractical as there was no way of maintaining temperature control during the reaction period.

In a second series of experiments an autoclave was used to provide both better temperature control and higher peak temperatures, the attainment of such higher temperatures being important when soy flour was used as the proteinaceous matrix material. Since the autoclave had no mechanical stirrer, the ingredients to be combined were intimately mixed in a separate vessel which was then placed in the autoclave.

In Example 4, 131 grams of water and 10 grams of 50% sodium hydroxide solution were intimately mixed with 170 grams of casein in a stainless steel bowl. The latter was then placed in an autoclave and heated for 15 minutes at 225° F. (4 psig) to produce a sticky, viscous, plastic, non-flowable but shapeable, semi-solid mass, the temperature being about 180° F. The bowl and contents were removed from the autoclave and 30 grams of oil of orange was added to the mix, with very vigorous stirring, until there was no visual evidence of free oil, the mass being sticky and having a translucent, gel-like appearance.

After cooling to room temperature, the mix viscosity increased to a taffy-like consistency, and while still soft and pliable, it was sliced into 1/16" thick strips, using a bacon slicer. The screened product was air dried at room temperature for 1 day to a moisture content of 6% by weight. The strips were ground in a Raymond Mill to a size such that substantially all passed through a 5 mesh U.S. Standard screen.

Separate portions were analyzed (by distillation) after various time intervals of storage at 100° F. It was found that after two weeks of such storage over 97% of the essential oil remained in the product. In Example 4, TABLE II, where the autoclave was used, it was possible to increase the temperature to 180° F. and under these conditions less water was used (40%) than when the silent cutter was used (51% water). By making a heavy plastic mass in the autoclave 93.3% of the essential oil used was found in the product. The stability was remarkably good; 97% of the oil was retained after two weeks storage. This is in contrast to the lower conversion and somewhat lower stability and significantly higher levels of water required in the silent chopper procedure. The data for the oil of orange run (Example 4) are presented in TABLE II as are data for a casein run in which oil of sage (Example 8) was the encased material.

TABLE II

| | AUTOCLAVE | | | | |
|---|---|---|---|---|---|
| Example | 4 | 5 | 6 | 7 | 8 |
| Casein (gms) | 170 | — | — | — | 127 |
| Soy Flour (gms) | — | 170 | 237 | 270 | 63 |
| Water (gms) | 131 | 110 | 170 | 214 | 139 |
| Water (%) | 40 | 36 | 40 | 42 | 40 |
| Oil of Orange (ml) | 30 | 30 | — | — | — |
| Oil of Sage (ml) | — | — | 12.5 | — | 10.0 |
| Oil of Nutmeg (ml) | — | — | — | 30 | — |
| 50% NaOH (gms) | 10 | — | — | 3.5 | 7.5 |
| Essential Oil (%)* | 15 | 12.8 | 4.6 | 8.9 | 4.6 |
| Essential Oil Content of Ground Dried Product (%)* | 14.0 | 8.8 | 3.6 | 7.5 | 4.0 |
| Fraction of Essential Oil Used Found in Dried Product (%) | 93.3 | 68.8 | 79.1 | 84.3 | 87.0 |
| Essential Oil Retained in Product After 2 weeks' Storage of 100° F. | | | | | |
| (%)* | 13.6 | 8.8 | 3.6 | 7.0 | 4.0 |
| (%)** | 97 | 100 | 100 | 93 | 100 |

*Based on combined weight of protein material plus essential oil
**Based on essential oil content of ground dried product as originally produced In Example 5 soy flour was used as the encasing agent following the same general procedure as in Example 4 except that less water was used and that the oil of orange was pre-heated to 180° F. before being added to the hot mixture of water and soy flour. After incorporation of the oil and agitating, the sticky mass was shaped into a ⅛" patty, slided into strips, and air dried to 6% moisture, and then ground. There was substantially no loss in essential oil upon storage of the ground material at 100° F. This was a marked improvement over Example 2 and 3 in which the silent cutter was used. The improvement is attributable to the more effective heating of the soy flour in the autoclave.

Examples 6 and 7 are similar to Example 5 except that oil of sage and oil of nutmeg were used as the encased agent. Again, the stability of the final ground product was excellent, there being over 90% retention of the oil even after 2 weeks' storage at 100° F.

The experiments carried out with the silent cutter and with the autoclave established conclusively the practical feasibility of the process of the invention. In each system studied essential oils were effectively encased in a proteinaceous matrix in a semi-solid, mechanically-worked mass without any need to form an initial solution. Additionally, it was demonstrated that the water required was markedly less than had heretofore been considered necessary. The efficacy of applicants' method is predicated on the utilization of minimal quantities of water in a system of high mechanical stress to produce a microdispersion in a natural polymer matrix.

USE OF A PLOW MIXER

In another series of runs, a Littleford* plow mixer, pilot commercial equipment ideally suited for the practice of the invention, was used. This equipment, utilizing a combination of plows and screw agitators, is capable of exerting tremendous shear forces to mix semi-solid masses. First, water introduced into the Littleford was heated by application of steam to a surrounding jacket. The protein was then added and the mixture vigorously agitated for approximately 5 minutes to form a viscous semi-fluid mass. The agent to be encased was then added and agitation was continued for approximately 5 minutes. The heavy viscous mass was then discharged in suitable containers and passed over cooled rolls to form sheets which were partially dried to a moisture content of 20%. The partially dried product was then coarsely ground through a Comitrol before the final drying step.

*Littleford Bros., Inc., Cincinnati, Ohio

EXAMPLE 9

Encapsulation of Vitamin A Acetate

The process of the present invention was found to be an excellent procedure for making a free flowing stabilized Vitamin A. A plow mixer was used, with the following formulation:

| Casein | 22.8 lbs. | 43% |
|---|---|---|
| Water | 30 lbs. | 57% |
| 50% Sodium Hydroxide | 1.5 lbs. | |
| Vitamin A Acetate | 14.8 lbs. | 40% |

The water was brought to a boil in a Littleford plow mixer, followed by the addition of the alkali and casein to form a smooth viscous paste. The Vitamin A was then added and agitation was continued for 10 minutes. The product was sheeted and dried for about 10 minutes to 102° F. followed by grinding through an Urschel Mill using a ⅛" cutter, followed by final drying for 30 minutes at 120° F. In order to protect the Vitamin A, it was found best to make an initial grind when the product contained approximately 20% moisture, followed by final grinding to the desired mesh. Utilizing this procedure ensured a higher degree of protected encapsulation as determined by hexane solubility tests. The initial Vitamin A "concentration", in international units per gram, was 788,700 and after 6 weeks of storage at 37° C. the potency was 545,300 units per gram. This stability compared very favorably with the principal stabilized Vitamin A product on the market which is made by the far more complicated spray drying of gelatin solutions.

In each of Examples 10 through 12 and 14 of TABLE III casein was the encapsulating material used, the principal difference in these examples being the concentration of the essential oil (a range of about 15% to about 40% based on the combined weight of essential oil plus encapsulating material) and the concentration of water (about 25% to about 45% based on the total weight of materials).

In Example 13 soy flour was the encapsulating material, and the essential oil concentration waas 10.8%, based on the combined weight of essential oil plus encapsulating material. In Examples 10 through 13 the essential oil was orange terpenes; in Example 14, oil of peppermint.

Upon analysis it was found that the fraction of original essential oil incorporated in the product was highly satisfactory, being in the range of from about 75% to over 96%. After storage at two weeks at 100° F. in an open system, the percent of essential oil which remained encapsulated was excellent-about 72% to about 100%. In Examples 10 and 14, where the essential oil added was 20% and 17% respectively, the recovery in the finished ground product was 93 to 96% and the stability of the ground product was 87 to 100%. In Examples 11 and 12, where the essential oil added was significantly higher at 35 to 35.8%, the recovery (conversion into the product) was still in excess of 90% showing excellent encasement, but the stability was somewhat decreased.

Additional examples indicating the utility of plow mixers in the practice of the present invention are summarized in TABLE IV which describes the encapsulation of concentrated seasonings including oleoresin celery, oleoresin black pepper, oil of sage, weiner seasonings blend, and oleoresin turmeric. It is an important feature of the invention that it is possible to prepare final seasoning products which have markedly enhanced flavoring capabilities as compared with their "natural" counterparts and as compared with commercial dry soluble seasonings. In TABLE IV the relative strength of each seasoning prepared in accordance with the invention as compared with commercial dry soluble products is indicated by the designation of a numeral and X such as 3X, 5X and 10X showing the factor by which the seasoning of the invention exceeds the "strength" of the "soluble" seasoning. The concentrates of the invention avoid objectionable features of soluble seasonings consisting of an oleoresin applied to salt or to sugar. The application of more than a relatively small amount of the oleoresin to such carriers produces sticky products or causes the essential oil to weep into the packaging material. As a result, the maximum level of oleoresin possible in the prior art soluble seasonings is only about 5%. A concentration of 30% or more is possible in accordance with the present invention. Another disadvantage of conventional soluble seasonings is that the essential oil merely stays, unprotected, on the surface of the carrier and, since the essential oil is relatively volatile, unless special packaging is used, flavor components are lost. The products of the subject invention obviate premature loss of volatiles.

TABLE III

| | LITTLEFORD (Plow Mixer) Essential Oils | | | | |
|---|---|---|---|---|---|
| Example No. | 10 | 11 | 12 | 13 | 14 |
| Casein (lbs) | 46 | 41.0 | 41.0 | — | 22.8 |
| Soy Flour (lbs) | — | — | — | 27 | — |
| Oil of Peppermint (lbs) | — | — | — | — | 4.67 |
| Orange Terpenes (lbs) | 11.0 | 24.2 | 24.2 | 3.3 | — |
| Water (lbs) | 38.0 | 31.7 | 23.8 | 20 | 19.1 |

TABLE III-continued

| | LITTLEFORD (Plow Mixer) Essential Oils | | | | |
|---|---|---|---|---|---|
| Example No. | 10 | 11 | 12 | 13 | 14 |
| Water (%) | 44 | 33 | 27 | 40 | 40 |
| 50% NaOH (gms) | 3 | 2.4 | 2.4 | 0.25 | 1.5 |
| Essential Oil (%)* | 20.0 | 37.2 | 37.2 | 10.8 | 17.0 |
| Essential Oil Content of Ground Dried Product (%)* | 18.5 | 35.8 | 34.0 | 8.4 | 16.3 |
| Fraction of Oil Used Found in Dried Product (%) | 93 | 96 | 91 | 77 | 96 |
| Essential Oil Retained in Product after 2 Wks' Storage at 100° F. (%)* | 18.5 | 28.0 | 24.5 | 6.2 | 14.1 |
| (%)** | 100 | 78 | 72 | 74 | 87 |

*Based on combined weight of protein material plus essential oil
**Based on essential oil content of ground dried product as originally produced.

The concentrated flavor and spice products of the present invention make possible marked economies in the cost of freight and warehousing. The stable and free-flowing products are a very advantageous "compromise" between pure essential oils or oleoresins, which are most difficult to use, and soluble seasonings which are limited as to strength and have other disadvantages.

The stability of each concentrate ground through a 60 mesh screen was determined and found to be excellent, there being substantially no loss in strength after storage for extended periods of time. In Example 16, dealing with oleoresin black pepper, the essential oil content initially was 4.1% and after 14 days incubation at 100° F., 4.1% essential oil was found, which shows almost perfect encapsulation. In addition, the fixed oleoresin was effectively encased since essentially none of the fixed oleoresin could be extracted with hexane.

In still another series of experiments (TABLE V) the Littleford plow mixer was used to encase minerals, vitamins and sweetening agents in a proteinaceous matrix, specifically casein. In Example 20, 2.5 pounds of ferrous sulfate·7H$_2$O was combined with 22.8 pounds each of casein and water and after enrobing the iron followed by drying, the resulting product ground through a 60 mesh screen. Tests carried out with the product of Example 20 prove the effectiveness of the encasement or enrobing technique of the invention as a means to protect or otherwise to isolate an encased material in a proteinaceous matrix. The material used in this study was powdered product ground through 60 mesh and containing 10% by weight of ferrous sulphate in casein.

TABLE IV

| | LITTLEFORD (Plow Mixer) Seasonings | | | | |
|---|---|---|---|---|---|
| Example No. | 15 | 16 | 17 | 18 | 19 |
| Seasoning | Oleoresin celery | Oleoresin Black Pepper | Oil of Sage | Weiner Essential Oil and Oleoresin Blend | Oleoresin Turmeric |
| Casein (lbs.) | 25 | 25 | 20 | 22.2 | 20 |
| Water (lbs) | 20.9 | 20.9 | 16.75 | 18.6 | 16.75 |
| Water (%) | 42 | 41 | 38 | 36 | 36 |
| 50% NaOH | 1.6 | 1.6 | 1.3 | 1.4 | 1.3 |
| Oleoresin Celery | 3.88 pints | | | | |
| Oleoresin Black Pepper | | 6.04 lbs. | | | |
| Oil of Sage | | | 5.5 pints | | |
| Weiner Seasoning | | | | 9.4 pints | |
| Oleoresin Paprika | | | | 1 pint | |

TABLE IV-continued

| | LITTLEFORD (Plow Mixer) Seasonings | | | | |
|---|---|---|---|---|---|
| Example No. | 15 | 16 | 17 | 18 | 19 |
| Seasoning | Oleoresin celery | Oleoresin Black Pepper | Oil of Sage | Weiner Essential Oil and Oleoresin Blend | Oleoresin Turmeric |
| Oleoresin Turmeric | — | — | — | .14 ozs. — | 10 lbs. |
| Seasoning (%)* | 13 | 19 | 22 | 33 | 33 |
| Strength Ratio (compared with Commercial Dry Solubles) | 3X | 3X | 10X | 5X | 3X |
| Essential Oil Retained in Product After 2 wks. storage at 100° F. (%)** | 95 | 95 | 93 | 95 | |

*Based on combined weight of protein material plus seasoning
**Based on essential oil content of dried product as originally produced The tests described are based upon the fact that a metal such as ferrous iron greatly accelerates peroxide formation in fats. In order to evaluate the pro-oxidant effect of that iron present in 10 grams of powdered product made in accordance with the invention, five grams of lard, containing no antioxidant, was melted and blended uniformly with 85 grams of wheat flour, after which the 10 grams of the Example 20 product was blended in. The sample (Sample 1) thus prepared was compared with two control samples prepared as follows:

In the first control sample (Sample 2) 5 grams of the same lard product was melted and blended uniformly with 85 grams of the same wheat flour product. One gram of ferrous sulphate and 9 grams of casein (using the same ferrous sulphate and the same casein used in Example 20) were uniformly blended with the lard and the wheat flour to form a control sample.

In the second control sample (Sample 3) 5 grams of lard was melted and blended uniformly with 85 grams of wheat flour. This was blended with 10 grams of casein to provide a control sample containing no ferrous sulphate. The compositions of the test sample and the two control samples are set forth in TABLE V.

TABLE V

| | PLOW MIXER (LITTLEFORD) Minerals, Vitamins, Sweeteners | |
|---|---|---|
| Example No. | 20 | 21 |
| Agent | FeSO$_4$ . 7H$_2$O | Xylitol |
| Casein (lbs) | 22.8 | 10 |
| Water (lbs) | 22.8 | 8 |
| Water (%) | 47 | 12 |
| 50% NaOH (lbs) | — | 0.6 |
| Agent Used (lbs) | 2.5 | 50 |
| Agent Used (%)* | 9.0 | 83 |

*Based on combined weight of protein material plus agent

One batch of each of the three blends was filled to a depth of about ½" in each of separate, open 5"×7", aluminum trays, and the trays stored for periods of 4, 6, 10 and 26 days in an incubator at 100° F. At each of the indicated time intervals a 25 gram sample of each blend was extracted with chloroform and the peroxide value of the extracted fat determined (AOAC 28.022, 125th edition, 1975; meq.peroxide/kg oil or fat). The peroxide values found are shown in TABLE V-A.

The samples are examined for odor as an indication of the development of rancidity in the fat. The results of these olfactory tests are also recorded in TABLE V-A.

TABLE V-A

| Sample No. | (1) | (2) | (3) |
|---|---|---|---|
| Length of Storage 100° F. | Blend having Proteinaceous Extrudate with Ferrous Sulfate Therein | Control Blend with Ferrous Sulfate | Control Blend Without Ferrous Sulfate |
| 4 Days | 3.4 | 13.7 | 3.4 |
| 6 Days | 3.3 | 14.2 | 0 |
| 10 Days | 5.2 | 18.8 | 0 |
| 20 Days | Sweet Odor | Very Rancid Odor | Sweet Odor |

It was found that the control blend of ferrous sulfate (Sample 2) had already developed a rancid note after only six days of storage, the odor becoming more evident after 10 days of storage and being very marked after 26 days of storage. The Example 20 blend (Sample 1) showed only a low level of peroxide formation after 10 days of storage. The lard still had a good odor and showed no evidence of rancidity.

In a second series of runs, a portion of each of the same three blends was sealed in each of separate pint jars and the jars stored in an incubator at 100° F. After 11 days, the control belnd, without ferrous sulfate (Sample 3), had a peroxide value of 3.3, the same peroxide value was obtained for the blend made with the Example 20 material (Sample 1). The control blend which contained ferrous sulfate (Sample 2) had a peroxide value of 17.1 after 11 days storage and exhibited a rancid odor.

The above data established conclusively that the product prepared in accordance with the practice of the invention possesses enhanced stability characteristics under the conditions described.

In Example 21, a sweetening agent, xylitol, was encased in casein. 50 pounds of xylitol was mixed with 10 pounds of casein and 8 pounds of water and the resulting slurry dried and ground to pass through a 100 mesh screen. The final product exhibited a slower sweetness release in chewing gum. Similar runs with similar results were carried out with the sweeteners Sorbitol, Mannitol, and cane sugar.

The method of the invention has been found to be useful as a technique for encapsulating material in gelatin. It will be appreciated that the procedure is substantively different from the prior art utilization of gelatin solutions as encapsulating media. In the instant case, the gelatin is used with a relatively small amount of water rather than with an excess of water to produce a solution.

In a typical procedure according to the practice of the invention, 22 pounds of gelatin was mixed with about 13 pounds of water in a Littleford plow mixer heated to a temperature of about 200° F. About 5½ pounds of essential oil (orange oil terpenes) was then added and stirring continued for an additional five minutes. The resulting product, having a very heavy taffy-like consistency, was cooled on chilled rolls. The material was partially dried for 15 minutes at 120° F. and then passed through a Comitrol grinder (0.120" cutting head), the coarsely chopped material dried for 30 minutes at 120° F., and the dried material ground in a Raymond Mill. The essential oil content of the particulate material was 18.7%. The relevant data are set forth in TABLE VI.

The preferred procedure is partially to dry the material so that a Comitrol or equivalent grinder can be used to reduce the particle size of the material as far as possible before drying is completed. In this manner, the fracture points of the protein are minimized, the retention properties are improved, and stability of products such as Vitamin A is enhanced.

TABLE VI

| Encapsulation in Gelatin | |
|---|---|
| Example | 22 |
| Agent Used | |
| (Orange Oil Terpenes) (lbs) | 5.5 |
| (%)* | 20 |
| Gelatin (lbs) (175 Bloom) | 22 |
| Water (lbs) | 13 |
| (%) | 32 |
| Essential Oil in Final Product (%) | 18.7 |
| Fraction of Oil Used Found in | |
| Final Product (%) | 94 |

*Based on combined weight of gelatin plus orange oil terpenes

The method of the invention may be carried out as a continuous process, a Baker-Perkins Ko Kneader Model MPM twin screw continuous mixer being suitable. This machine includes a feed and helical screw section, a series of orifice plugs within a high shear intensive mixing section, and a screw discharge section. The mixer is jacketed and the barrel temperature was 200° F. The product was discharged at 180°-195° F. at a rate of two pounds per minute. In Example 23 casein, water and sodium hydroxide were fed into the helical screw section at the rate of 0.98 lb./minute, 0.62 lb./minute and 0.058 lb/minute respectively and orange terpenes were fed into the intensive mixing section at a rate of 0.21 lb/minute. The product having a dry, translucent, grainy appearance was passed through chilled rollers to produce a dough-like sheet. This was dried, ground and screened, and analyzed, the data being summarized in TABLE VII. The results indicate that over 80% of the essential oil was encased in the casein to provide a product having excellent retention properties and stability, over 97% of the oil being retained after 2 weeks storage at 100° F.

In a similar experiment (Example 24) in which the essential oil concentration was increased to 30%, over 85% of the oil was incorporated into the product and over 90% of the incorporated oil was retained in the product after 2 weeks' open storage at 100° F. The above two examples show that excellent microdispersions of oil in a natural polymer matrix can be accomplished in a simple continuous process.

TABLE VII

| Continuous Encasement Process | | |
|---|---|---|
| Example No. | 23 | 24 |
| Casein (lbs/min.) | 0.98 | 0.75 |
| Water (lbs/min.) | 0.62 | 0.44 |
| 50% NaOH (lbs/min.) | 0.058 | 0.044 |
| Oil of Orange (lbs/min.) | 0.21 | 0.16 |
| Essential Oil Content | | |
| of Ground Dried Product (%)* | 16.2 | 26.5 |
| Essential Oil Retained in | | |
| Product After 2-Weeks' | | |
| Storage at 100° F. (%)* | 15.8 | 24.2 |
| (%)** | 97.5 | 91.3 |

*Based on combined weight of protein material plus essential oil
**Based on essential oil content of dried ground product Chemically modified starches such as food grade dextrin (Capsul* brand) have been found particularly suitable as encapsulating agents in the practice of the present invention. Various seasoning and flavoring agents as well as related chemical compositions such as beef extracts and grape juice concentrates have been effectively encapsulated in such chemically modified starch materials. The following detailed procedure for the encapsulation of acetaldehyde is typical. *National Starch and Chemical Corp.

In general, the procedure is to prepare a homogeneous paste of the modified starch and water, followed by the addition of the material to be encapsulated. In contrast with the relatively high temperatures used in spray drying processes, the process of the present invention uses effectively almost any temperature and it is possible to dry under conditions such that delicate flavoring agents will be retained to a much greater degree.

EXAMPLE 25

Encapsulation of Acetaldehyde

The effective encapsulation of the flavor adjunct acetaldehyde, in accordance with the process of the present invention, is indicative of the effectiveness of the process for encasement of low boiling liquids. Acetaldehyde, which is water soluble, boils at about 68° F. Extensive work has been carried out and many patents are directed to procedures which purport to encapsulate acetaldehyde, but the conversions into the ultimate product are extremely low, ranging from about 1% to about 3%. In marked contrast, following the method of the subject invention, it has been found possible to convert 25% or more of the highly volatile material into the final encapsulated product. The following formulation was used:

| Dextrin (Capsul* Brand) | 400 grms. |
|---|---|
| Water | 200 ml. |
| Acetaldehyde | 100 ml. |

*National Starch and Chemical Corporation

The cooled acetaldehyde was first added to the modified starch and mixing carried out in a fume hood. Water was added and the mixing was vigorously continued to provide a very heavy homogeneous paste. This paste was placed on trays in a thin layer and allowed to dry overnight. The resulting dry product was ground to pass a 30-mesh screen and then analyzed for acetaldehyde. The product was found to contain 4.9% of acetaldehyde, representing a 25% conversion. After incubating the dried product for five days at 100° F., the concentration of acetaldehyde remaining in the product was 3.9%, establishing good stability for the product. The analyses were carried out on a product which had been ground to pass a 30-mesh, with 20% on a 40-, 37% on an 80, and 33% passing through a 100-mesh screen.

EXAMPLE 26

Encapsulation of Pine Oil

There is much commercial interest in encapsulating odor agents to be incorporated in cat litter products. In accordance with the present invention it has been found that pine oil may be effectively encapsulated for use in such products. The following formulation was employed.

| Dextrin (Capsul brand) (Modified Starch) | 400 gms. |
|---|---|
| Pine oil (Monsanto Pine Forest 14049 | 100 ml. |
| Water | 132 ml. |

The percentage of water, based upon the total weight of water and modified starch was 25%, and the essential oil based on the total weight of essential oil and encapsulating material was 20%.

The pine oil was mixed with the modified starch. Boiling water was then added and the material was worked into a very smooth paste which was then formed into thin sheets and dried for 1 hour at 110° F.

After further drying at about 140° F., the product was ground through a Raymond Mill to pass through a 20 mesh screen. Upon analysis, the dried ground material was found to contain 16.3% of pine oil (81% conversion). 16.0% of Pine Oil remained in the product after storage for 3 months at 100° F., indicating excellent stability.

EXAMPLE 27

Encapsulation of Oil of Cloves (and Oil of Cinnamon)

Clove is sold in the form of a natural spice, as an essential oil, and also as a soluble seasoning in which about 6% of the essential oil is applied to salt or sugar. When utilizing the process of the present invention, it is possible to produce a free-flowing, stabilized product with 20% of essential oil. One pound of this product has the flavoring capability of 2 pounds of natural spice or four pounds of soluble seasoning.

A Littleford mixer was used in conjunction with the following formulation:

| Dextrin (Capsul) | 20 lbs. |
|---|---|
| Water | 6 lbs. |
| Oil of Clove | 5 pts. |

The water based upon the total weight of water and modified starch was 23%, and the oil of cloves based upon the total weight of oil and encapsulating medium was 20%. The water was brought to a temperature of about 205° F. and the modified starch was then added. About 1 minute later the essential oil was added and agitation continued for 10 minutes. The product was then discharged from the Littleford, at a temperature of about 170° F. It was noted that the amperage on the plow was 5.0 and the chopper amperage was 6.0. The homogeneous paste was discharged from the Littleford as a viscous mass and sheeted well on cooled rollers. The sheets were then dried for 20 minutes at 110° F. and for an additional 45 minutes at 140° F.

In contemplation of the use of the product in tea, the final product was ground to pass through a 5 mesh and to be retained on a 10-mesh screen. Upon analysis the product was found to contain 19.5% of oil of clove indicating about 98% conversion. After three months' storage at 100° F., the oil content was found to be about 20%, indicating excellent stability.

Encapsulated Oil of cinnamon was made following essentially the same process described above. Again, excellent conversion and stability were achieved.

EXAMPLE 28

Encapsulation of Butter Flavor

The suitability of the method of the invention as a technique for encapsulating sensitive and volatile flavor elements was further demonstrated by work carried out in the encapsulation of butter flavor, containing diacetyl and butyric acid. These chemical agents are ordinarily lost in conventional spray drying. The following formulation was used in the encapsulation method of the instant invention.

| Dextrin (Capsul) | 13½ lbs. |
|---|---|
| Butter flavor | 4½ lbs. |
| Water | None, per se |

The butter flavor used contained 40% by weight of water, an amount found sufficient to provide a heavy homogeneous paste (water concentration 12%, based upon total of the water and the encapsulating material.)

In some of the procedures carried out in the practice of the invention, particularly with aqueous liquid flavors, it was found advantageous first to heat the modified starch in the dry form. In the instant experiment, the modified starch was heated to 190° F. whereupon the butter flavor warmed to 130° F. was added, and heating discontinued and cooling water introduced into the jacket of the Littleford mixer. Mixing was continued for about 10 minutes and the temperature of the resulting viscous paste, upon discharge from the mixer, was 125°–130° F. The product sheeted well on cooled rollers. The sheets were immediately chopped in a Urschel using a 0.06 cutter and the resulting material was dried on a shelf drier at 100° F. for 1½ hours. Finally, the product was ground to pass a 40-mesh screen.

The theoretical calculated butyric acid concentration of the butter flavor was 12.5%, and the ground dried product was found to contain 12.2%, indicating excellent conversion. After storing for 5 days at 100° F., the butyric acid concentration was found to be 10.1%, indicating good storage stability. The diacetyl content of the ground butter flavor was 1.27% and after storage for 14 days at 100° F., the concentration was 1.16%, indicating excellent storage stability.

EXAMPLE 29

Encapsulation of Grape Juice Concentrate

Some of the flavor compositions sold in the food industry take the form of paste rather than dry powders. Since high-temperature drying of such products causes substantial flavor loss, spray drying materially impairs the flavor profile.

In accordance with the practice of the invention it has been found feasible to encapsulate grape juice while retaining the critical flavor profile. The following formulation was used:

| Dextrin (Capsul) | 16½ lbs. |
|---|---|
| Grape Juice Concentrate | 5½ lbs. |
| Water | ½ lb. |

The grape juice concentrate contained 62.8% of water so that the 5½ lbs. used contained 3.4 lbs. water and the total concentration of water in the encapsulation system, based upon the weight of water and Dextrin was 19.0%. The percent of grape juice concentrate, based on the weight of the concentrate and the dextrin was 25%.

The dextrin was added to a Littleford plow mixer and steam then introduced into the jacket to heat the dry dextrin to 185° F. The grape juice concentrate, first warmed to 134° F., was added to the heated dextrin, and mixed for 10 minutes.

EXAMPLE 30

Encapsulation of Concentrated Lemon Juice

Lemon juice concentrate was effectively encapsulated using a process corresponding essentially to the process described with reference to the grape juice concentrate.

The concentrate was heated to about 120° F. before being added to the preheated Capsul. The Capsul, lemon concentrate and water mixture was processed for about 15 minutes in the plow mixer, discharged, sheeted and dried. The flavor profile of the final product was found to be excellent.

| Modified Starch (Capsul) | 25½ lbs. | 81% |
|---|---|---|
| Lemon Juice Concentrate | 8½ lbs. | 10% |
| Water | 13.6 ozs. | 19% |

EXAMPLE 31

Encapsulation of Cheese Flavor

In addition to encapsulating oils, oleoresins, solids, and liquids, the process of the subject invention has been found highly suitable for converting paste materials to a dry, particulate form, without distorting delicate flavor profiles. The remarkable effectiveness of the process is demonstrated with reference to the encapsulation of natural cheddar cheese flavor which contains 60% of moisture. The following formulation was used:

| Modified starch or dextrin (Capsul) | 20 lbs. |
|---|---|
| Cheddar cheese flavor | 10 lbs. |

The calculated concentration of water, based upon the total of water and encapsulated agents was 23%. The dry modified starch was heated to 200° F., and cheese flavor warmed to 118° F., was added to the plow mixer (Littleford) and agitated for 20 minutes. The resulting mass was quite viscous and the amperage on the plow was 12 while the chopper showed an amperage of 5. The product sheeted well and the sheets were dried for 1 hour at 100° F. and the product then chopped in a Urschel chopper using a 0.06 cutter. The drying was completed in 45 minutes at 100° F., whereupon the material was ground through a Fitz Mill to pass a 40 mesh screen.

EXAMPLE 32

Encapsulation of Annatto Food Color

The following formulation and procedure were employed:

| Modified starch (Capsul) | 1 lb. |
|---|---|
| Annatto powder | 1 lb. |
| Water | 9 ozs. |

The percentage of water, based upon the combined weight of water and modified starch was 36%.

The dried modified starch was heated to 185° F., boiling water was added to the Annatto powder to form a heavy paste, and the paste was then mixed with the heated Capsul. Mixing was continued and the heavy paste was transformed into a smooth product which sheeted well. The sheets were dried at 100° F. and then ground in a laboratory Raymond Mill to pass a 40-mesh screen. There was no perceptible color loss during the process.

EXAMPLE 33

Encapsulation of Oleoresin Turmeric

Oleoresin Turmeric has been effectively encapsulated using the process of the invention. The ultimate product is a dry powder which is readily dispersible in water but which may require the addition of a surfactant in order to solubilize the oleoresin product. The following formulation was used:

| Modified starch (Capsul) | 3.5 lbs. |
|---|---|
| Oleoresin Turmeric | 1.35 lbs. |
| Polysorbate 80 | 0.15 lbs. |
| Water | 0.88 lbs. |

The percentage of water, based upon the combined weight of water and encapsulating material was 20%, and the concentration of turmeric, based upon the combined weight of turmeric and encapsulating agent was 27%.

The Capsul was heated to 150° F. and the turmeric and polysorbate 80 were warmed until fluid and were then blended into the heated Capsul, followed by the addition of the water heated to 140° F. A heavy homogeneous paste was formed which sheeted well. The sheets were partially dried followed by sizing through a Urschel, and were then dried to a moisture content of 8%. The final product was a free-flowing powder with good color stability. Upon addition of water, the powder dissolved and a clear aqueous solution was formed.

EXAMPLE 34

Encapsulation of Beef Extract

Beef extract, a very thick paste material, is readily converted, in accordance with the practice of the instant invention, to a free-flowing easy-to-use stable product. The following formulation was employed:

| Modified starch (Capsul) | 400 gms. |
|---|---|
| Beef extract | 200 gms. |
| Water | 70 ml. |

The water concentration, including that contained in the beef extract, was 24.5%, based upon the combined weight of water and encapsulating material. The modified starch was heated to 165° F., and the beef extract was worked into the mass to provide a heavy, smooth, homogeneous paste. This product was then sheeted and dried. After grinding, this product was free-flowing with a high concentration of stable beef extract flavor. Protein hydrolysates may be incorporated in this blend, either alone or in combination with beef extract to give non-hygroscopic, free-flowing beefy flavors.

EXAMPLE 35

Encapsulation of Artificial Potato Flavor

In view of the tremendous growth in the processed potato industry, there has been extensive interest in the development of improved potato flavors. While there are excellent liquid artificial potato flavors on the market, the spray dried encapsulated potato flavors have flavor profiles which are substantially distorted. It has been found that greatly improved dry potato flavors are produced in accordance with the practice of the present invention. The following formulation was used:

| Modified starch (Capsul) | 800 gms. |
|---|---|
| Artificial potato flavor | 200 gms. |
| Water | 200 gms. |

The percent of water, based upon the combined weight of water and modified starch was 20%, while the concentration of liquid potato flavor, based upon the combined weight of flavor and encapsulating agent was 20%. The modified starch was heated in a steam kettle to about 155° F. and the potato flavor then mixed into the warmed Capsul followed by addition of water, previously heated to 140° F. The resulting heavy paste was blended to a smooth heavy batter and the product then sheeted and dried for 45 minutes at 110° F. followed by sizing through a Urschel chopper. The product was then dried for an additional 45 minutes at 110° F. and then ground to pass a 40-mesh screen. Upon taste evaluation, it was found that the encapsulated product produced had excellent potato flavor, quite comparable to the initial liquid flavor material used. The flavor was found to be markedly superior to that obtained in the spray drying process of the prior art.

Commercially available gums may also be used effectively as the encapsulating material in the practice of the present invention. The various gums have different physical properties, and not all gums are equally suitable. Typical of acceptable gums is gum acacia. As in the case of modified starch systems, it is necessary to establish an appropriate balance between the water concentration and the encapsulating medium so as to ensure maximum conversion of the ingestible agent as a microdispersion in the encapsulating medium and to achieve maximum stability of the final product. In general, the water concentration in the gum acacia systems is somewhat higher than that found optimum for the modified starches.

A series of compounds was prepared using gum acacia as the encapsulating agent for various ingestible materials including orange terpenes, fixed fats, banana flavor, diacetyl, and perfume. The runs are summarized in examples, and the following description is typical of the general procedure.

EXAMPLE 36

Encapsulation of Orange Terpenes

Using a Littleford* plow mixer, a mixture of 20 pounds of gum acacia, 12 pounds of water and 5 pints of orange terpenes (20%, based on essential oil plus gum) was heated and processed, the product temperature upon discharge from the apparatus being 140° F. and the viscosity in excess of 2 million centipoises. On sheeting this material on chilled rolls, the sheets, though somewhat thin and soft, but could be handled. After partially drying for about 5 minutes at 110° F., the sheets were chopped through a 0.06" cutter to provide a coarsely ground material. This was then dried for an additional 35 minutes at 110° F. to a moisture content of 7.6%. The ground product was found to contain 19% essential oil, showing excellent conversion. After incubation at 100° F. for four days, the essential oil remaining in the product was 14% or about 75% of the material originally converted.

*Littleford Bros., Inc. Cincinnati, Ohio

Several experiments were carried out with gum acacia but using lower and higher water concentrations. These data indicate the effect of water concentration variation on the viscosity of the system, the percent of oil converted into the encapsulation product, and the stability of the ultimate product.

EXAMPLE 37

Encapsulation of Fixed Fat

Gum acacia was found to be an excellent encapsulating medium for the encasement of fixed fat such as lard. In a typical procedure, 12.8 pounds of water was heated in a Littleford plow mixer and 32 pounds of gum acacia added. After about 5 minutes of mixing, 8 pounds of melted lard was added and the mixing continued for about 6 minutes after which the fat was discharged from the apparatus, the temperature being about 180° F. The product was then sheeted and dried at 140° F. followed by grinding to provide a free-flowing powder. The run establishes that it is feasible to produce free-flowing encapsulated fats utilizing a gum acacia encapsulating material and a low percentage of water. The ability to convert fats to such free-flowing powders utilizing a minimum of water in the encapsulation process offers many commercial advantages over the conventional procedures which have been used in the past.

EXAMPLE 38

Encapsulation of Diacetyl

In practicing the invention, gums have also been used effectively as encapsulating materials for the encasement of banana flavors, diacetyl, and perfume. In the encapsulation of diacetyl, the formulation used was:

| Gum acacia | 20 lbs. |
|---|---|
| Water | 11 lbs. |
| Diacetyl | 5 lbs. |

Diacetyl, a volatile water-soluble flavor found largely in butter flavors, boils at 180° F. The process of the invention permits encapsulation with minimal loss of the diacetyl. In this system shown, the percent of water, based on the weight of gum and water is 35%, while the percent of diacetyl, based on the weight of gum plus diacetyl is 20%. The water was added to a Littleford plow mixer and heated to 120° F., after which the gum acacia was added and the temperature of the homogeneous gum paste brought to 130° F. The diacetyl was added and agitation continued for 20 minutes to form a very smooth emulsion paste. Upon discharge from the apparatus at a temperature of 110° F., the paste was found to sheet readily on a cool roll. After partial drying at room temperature for 1 hour, the product was chopped in a Comitrol, (Urschel) using a 0.18 cutter, followed by drying. The dry product was then ground on a Fitz mill and the material passed through a 40-mesh screen with 32% on a 60 mesh and 27% through an 80-mesh.

The dried ground product was found to contain 12.4% of diacetyl (62% conversion). After storage for 23 days at 100° F., the diacetyl content was 8.9%. In conventional encapsulation, using spray drying, much greater losses are the rule.

EXAMPLE 39

Encapsulation of Perfume

The versatility of the invention is in that it is possible to encapsulate a temperature-sensitive agent and to end up with essentially the same odor and flavor profile as contained in the starting material. For example, the process has been found uniquely effective for the encapsulation of perfumes. In a typical formulation described below, gum acacia was used as the encapsulating material.

| | |
|---|---|
| Gum acacia | 15.0 lbs. |
| Water | 9 lbs. |
| Perfume | 5 lbs. |
| Mineral oil | 5 lbs. |
| Methyl paraben | 22.7 grams |
| Propyl paraben | 2.27 grams |

The percent water based on the total weight of water and gum was 36%, and the percent perfume based on the weight of perfume plus encapsulating agent was 20%. The water was first brought to a boil in a Littleford mixer and the preservatives and gum acacia added. Three minutes later the perfume was added, and heating discontinued. Mixing was continued for an additional five minutes after which the mineral oil was added and mixing continued for an additional 8 minutes. It was noted that the amperage on the plow was 5.0 and the amperage on the chopper within the range of 5.5 to 6.0. The product, at a temperature of 165° F., was transferred to a container as a viscous homogeneous paste. The paste sheeted readily on a cooled roller and the sheets were then dried for 1½ hours at 100° F. The brittle dried sheets were ground to pass a 40-mesh screen. Upon analysis, it was found that the essential oil contained in the finished product was 21.7%. After 14 days' storage at 100° F. the essential oil content remained unchanged, indicating remarkable stability.

A parallel experiment was conducted in which the same formulation was used except that a solution was prepared and the product was spray dried. The essential oil content of the spray dried product was 17% as contrasted with the 21.7% achieved in the process of the subject invention. It is clear that the novel method of the invention is markedly superior to the prior art spray drying technique.

EXAMPLE 40

Encapsulation of Banana Flavor

The encapsulation of banana flavor utilizing the process of the invention is an excellent example of the value of the process for the encasement of delicate materials. Banana flavor contains many volatile fruity esters which are ordinarily lost in a spray drying process. The following formulation was used:

| | |
|---|---|
| Gum acacia | 16 lbs. |
| Water | 8.8 lbs. |
| Banana flavor | 4 lbs. |

The percent of water based on the total weight of water and gum was 35% and the percent of banana flavor, based on the flavor and gum was 20%. The gum acacia was heated to 150° F. and the steam then turned off and hot water introduced into the jacket to maintain temperature. The banana flavor was then added followed by the additional water previously warmed to 140° F. A very viscous heavy paste formed and, after 11 minutes of agitation the product was discharged at a product temperature of 124° F. The product was found to sheet well on the rolls and was partially dried at 110° F. for 15 minutes, and passed through a Urschel chopper using first a 0.12 cutter and then an 0.06 cutter. The chopped material was then dried for an additional 30 minutes at 100° F. and the dried material then ground using a Fitz mill to provide a product essentially all of which passed through a 40-mesh screen. Taste evaluation tests on the encapsulated dried product for comparison with original banana flavor, on an equivalent flavor basis, showed essentially the same flavor profile, indicating minimal losses of volatile components.

EXAMPLE 41

Gums other than gum acacia may be used in the practice of the present invention. For example, gum karaya, although a much more viscous gum than gum acacia, was used effectively for the encapsulation of orange terpenes.

| | |
|---|---|
| Gum karaya | 20 lbs. |
| Water | 25 + 3 lbs. |
| Orange terpenes | 5 pints |

The calculated concentrations is 55% of water based on the weight of gum and water, and 20% terpenes, based upon the combined weight of terpenes and gum.

Following the general process, after 2 minutes of agitation, it was found that the product was thicker and more lumpy than desired and that the chopper was overloaded. The run was continued using only the plow. Additional water (3 pounds) was added to a total of 28 pounds (64% by weight). While the load on the chopper was still excessive, the agitation system worked effectively to provide a smooth paste. This was discharged at a temperature of about 120° F. and a viscosity well in excess of 2 million centipoises. The product was spread on trays and, after drying, was found to contain 16% of essential oil.

What is claimed is:

1. A method of encapsulation of an active agent as a microdispersion in a storage-stable enveloping matrix of an encapsulating material selected from the group consisting of chemically modified starches, gums, proteins and mixtures thereof, said method being characterized in that the encapsulating material is transformed thereby into a homogeneous, continuous, paste-like phase during processing thereof, said method comprising:

combining 1 part by weight of said encapsulating material with from about 1/25th part up to about 5 parts by weight of said active agent, and water in a limited amount of from about 10% up to about 50% by weight of water based upon the total weight of water, encapsulating material and active agent, but in an amount limited to ensure development and maintenance of a homogeneous, high-viscosity paste system during processing thereof, applying shearing stress and vigorous mechanical working and any necessary heat to said paste system to distribute said active agent throughout said encapsulating material as a microdispersion under processing conditions to avoid compaction and molding compression forces, thereby to prevent mechanical expulsion of said active agent from said encapsulating material, mechanically working said paste system into a very viscous mobile and formable mass having a viscosity in excess of about 50,000 centipoises and in which said active agent is distributed as micro particles throughout said homogeneous encapsulating material, mechanically shaping said mass without applying compression force effective to expel said active agent therefrom, thereby to provide a product of selectable physical configuration, and drying said product by a process other than spray drying to provide a storage-stable homogeneous matrix of said encapsulating material having protectibly and releasably enveloped therewithin said active agent as a micro-dispersed phase distributed substantially uniformly therethrough.

2. The method of claim 1 and further comprising the step of converting said product into a particulate of selectable mesh size and range.

3. The method as set forth in claim 2 wherein said active agent dispersed throughout said encapsulating material comprises particles sized in the range of from sub-micron to about 2 microns.

4. The method of claim 1 and further comprising the step of hydrating said product to effect a gradual release of said active agent from said matrix.

5. The method as set forth in claim 1 wherein said encapsulating material is selected from the group consisting of a modified starch, a gum and mixtures thereof, whereby upon exposure of said encapsulating material to an aqueous system, said active agent is rapidly released.

6. A butter flavor concentrate comprising butter flavor agents in the form of globules of said agents distributed as a micro-dispersion throughout a homogeneous protective matrix consisting essentially of a natural polymeric encapsulating medium derived from modified starch, said concentrate being characterized by balanced flavor properties correlated with the retention of volatile as well as fixed flavor elements of said flavor agents in the final product, and being produced in accordance with the method of claim 1.

7. A cheese flavor concentrate comprising a cheese flavor agent in the form of globules of said agent distributed as a microdispersion throughout a homogeneous protective matrix consisting essentially of a natural polymeric encapsulating medium derived from modified starch, and produced in accordance with the method of claim 1.

8. A flavor adjunct comprising from about 5 to about 25% by weight of acetaldehyde distributed as a microdispersion throughout a homogeneous protective matrix of a natural polymeric encapsulating medium derived from a modified starch, and produced in accordance with the method of claim 1.

9. A Vitamin A concentrate comprising Vitamin A distributed as a microdispersion throughout a homogeneous protective matrix consisting essentially of a natural polymeric encapsulating medium derived from a proteinaceous material, said concentrate being characterized by high stability of said encapsulated Vitamin A upon storage, and produced in accordance with the method of claim 1.

10. The concentrate of claim 9 wherein said proteinaceous material is casein and wherein said Vitamin A is present in a concentration of up to about 40% by weight based on the combined weight of casein and Vitamin A.

11. A flavor concentrate comprising an essential oil distributed as a microdispersion throughout a homogeneous protective matrix consisting essentially of a natural polymeric encapsulating medium derived from a proteinaceous material, said concentrate being characterized by high stability of said essential oil upon storage, and produced in accordance with the method of claim 1.

12. The concentrate as set forth in claim 11 wherein said proteinaceous material is casein and wherein said essential oil is oil of sage present in said matrix at a concentration of up to about 10 times that present in natural sage.

13. A slow release sweetener composition comprising xylitol distributed as a microdispersion throughout a homogeneous protective matrix consisting essentially of casein, and produced in accordance with the method of claim 1.

14. A citrus oil concentrate comprising a lemon juice concentrate in the form of liquid globules distributed as a microdispersion throughout a homogeneous protective matrix consisting essentially of a natural polymeric encapsulating medium derived from a modified starch, said concentrate being characterized by an excellent flavor profile conforming to the profile of the lemon juice concentrate used, and produced in accordance with the method of claim 1.

15. The method as set forth in claim 1 wherein said encapsulating material is a protein, and wherein said protein is characterized in that upon exposure to an aqueous system it undergoes hydration at a slow rate to effect a gradual release of said active agent encased therewithin.

* * * * *